(12) United States Patent
Asano et al.

(10) Patent No.: US 8,905,962 B2
(45) Date of Patent: Dec. 9, 2014

(54) ARTIFICIAL BLOOD VESSEL AND ACCESS PORT OF ARTIFICIAL BLOOD VESSEL

(75) Inventors: Takuji Asano, Tokyo (JP); Daisuke Yokoyama, Tokyo (JP); Yoshihiko Kinoshita, Tokyo (JP)

(73) Assignee: Nikkiso Co., Ltd. (JP)

( * ) Notice: Subject to any disclaimer, the term of this patent is extended or adjusted under 35 U.S.C. 154(b) by 0 days.

(21) Appl. No.: 13/496,739

(22) PCT Filed: Jun. 13, 2011

(86) PCT No.: PCT/JP2011/063480
§ 371 (c)(1),
(2), (4) Date: Mar. 16, 2012

(87) PCT Pub. No.: WO2012/002138
PCT Pub. Date: Jan. 5, 2012

(65) Prior Publication Data
US 2013/0103136 A1    Apr. 25, 2013

(30) Foreign Application Priority Data

Jul. 2, 2010 (JP) ................................ 2010-152035
May 27, 2011 (JP) ................................ 2011-118951

(51) Int. Cl.
| A61M 5/00 | (2006.01) |
| A61M 5/32 | (2006.01) |
| A61M 31/00 | (2006.01) |
| A61F 2/856 | (2013.01) |
| A61M 1/36 | (2006.01) |
| A61M 39/02 | (2006.01) |
| A61F 2/06 | (2013.01) |

(52) U.S. Cl.
CPC ............... *A61F 2/856* (2013.01); *A61F 2/064* (2013.01); *A61F 2002/061* (2013.01); *A61M 1/3655* (2013.01); *A61M 39/0208* (2013.01); *A61M 39/0247* (2013.01); *A61M 2039/0223* (2013.01); *A61M 2039/0258* (2013.01); *A61M 2039/0261* (2013.01); *A61F 2/06* (2013.01)
USPC ................ 604/8; 604/175; 604/508; 604/513

(58) Field of Classification Search
CPC ..................... A61M 39/0208; A61M 39/0247; A61M 39/04
USPC ..................... 604/8, 9, 513, 167.02, 508, 175
See application file for complete search history.

(56) References Cited

U.S. PATENT DOCUMENTS 3,783,868 A * 1/1974 Bokros ...................... 604/891.1
3,826,257 A * 7/1974 Buselmeier ...................... 604/8

(Continued)

FOREIGN PATENT DOCUMENTS

JP         53-95592       1/1977
JP         54-39989 A     3/1979

(Continued)

OTHER PUBLICATIONS

International Search Report for International Application No. PCT/JP2011/063480, dated Aug. 23, 2011, with English translation.

(Continued)

*Primary Examiner* — Leslie Deak
(74) *Attorney, Agent, or Firm* — Cantor Colburn LLP

(57) ABSTRACT

An artificial blood has a trunk portion with both ends connected to blood vessels, and access branch portions and a shunt branch portion branched from the trunk portion. The access branch portions are disposed with a solid column-shaped access port that plugs these branch portions. The access port has a solid center portion and a tube-shaped peripheral portion disposed to surround the center portion. The peripheral portion is harder than the center portion and prevents the needle from deviating from the inside of the center portion. This enables a puncture to be easily made in a therapy in which a puncture is highly frequently made in a blood vessel.

9 Claims, 5 Drawing Sheets

(56) References Cited

U.S. PATENT DOCUMENTS

| | | | |
|---|---|---|---|
| 4,164,221 A | | 8/1979 | Bentley et al. |
| 4,318,401 A | | 3/1982 | Zimmerman |
| 4,654,033 A | * | 3/1987 | Lapeyre et al. ............... 604/175 |
| 5,092,849 A | * | 3/1992 | Sampson ..................... 604/175 |
| 5,306,255 A | | 4/1994 | Haindl |
| 5,562,617 A | | 10/1996 | Finch, Jr. et al. |
| 5,713,859 A | | 2/1998 | Finch, Jr. et al. |
| 5,755,780 A | | 5/1998 | Finch, Jr. et al. |
| 5,807,356 A | | 9/1998 | Finch, Jr. et al. |
| 6,007,516 A | | 12/1999 | Burbank et al. |
| 6,056,717 A | | 5/2000 | Finch et al. |
| 6,459,917 B1 | * | 10/2002 | Gowda et al. ................. 600/345 |
| 6,726,711 B1 | | 4/2004 | Langenbach et al. |
| 7,124,570 B2 | * | 10/2006 | Blatter et al. ................ 604/6.16 |
| 2005/0027234 A1 | * | 2/2005 | Waggoner et al. ............... 604/8 |

FOREIGN PATENT DOCUMENTS

| | | |
|---|---|---|
| JP | 57-20272 | 2/1982 |
| JP | 60-18175 | 1/1985 |
| JP | 52-12107 A | 8/1993 |
| JP | 9-510885 A | 11/1997 |
| JP | 2001-509061 A | 7/2001 |

OTHER PUBLICATIONS

First Examination Opinion Notice for Chinese Patent Application No. 201180032783.6, issued Mar. 18, 2014, with English translation.

Office Action for Taiwanese Patent Application No. 100122291, mailed Apr. 21, 2014, with English translation.

\* cited by examiner

ARTIFICIAL BLOOD VESSEL AND ACCESS PORT OF ARTIFICIAL BLOOD VESSEL

CROSS REFERENCE TO RELATED APPLICATIONS

This is a U.S. national stage of application No. PCT/JP2011/063480, filed on 13 Jun. 2011. Priority under 35 U.S.C. §119(a) and 35 U.S.C. §365(b) is claimed from Japanese Application Nos. 2010-152035, filed 2 Jul. 2010, and 2011-118951, filed 27 May 2011, the disclosure of which are also incorporated herein by reference.

TECHNICAL FIELD

The present invention relates to an access port that leads out liquid from an indwelling artificial blood vessel or that introduces liquid into the indwelling artificial blood vessel

BACKGROUND ART

In a blood extracorporeal circulation therapy such as hemodialysis and apheresis in which patient's blood is once taken out of a body and returned into the body again, it is necessary to frequently insert a needle into a blood vessel. If a puncture into a blood vessel is frequently performed, an aneurysm may be formed or vasoconstriction may occur. A blood access (blood vessel reaching method) has been proposed that uses an indwelling type apparatus capable of reducing the number of punctures into a blood vessel. In a blood access disclosed in Patent Document 1, a blood chamber connected through a cannula to a blood vessel includes a diaphragm, and a needle is inserted into the diaphragm to perform introduction of blood, etc., into the blood vessel, leading-out of blood from the blood vessel, etc., through this needle. Since the puncture is repeatedly made into the diaphragm, the damage to the blood vessel is alleviated.

PRIOR ART DOCUMENT

Patent Document

Patent Document 1: Japanese Patent Application Publication No. Hei09-510885

SUMMARY OF THE INVENTION

Problem to Be Solved by the Invention

When a puncture is made, if a direction of a needle deviates, it may become difficult for liquid to flow. Currently, a large proportion of punctures are performed by skilled healthcare professionals in hospital facilities. However, making a puncture accurately, safely, and easily is an important concern for patients performing home dialysis. A technique enabling a puncture to be made accurately, safely, and easily is desired in hospital facilities etc., as well.

It is an object of the present invention to provide an access port that enables a puncture to be made accurately, safely, and easily.

Disclosure of Invention

According to the present invention, an access port is provided that is disposed on a branch portion of an artificial blood vessel. This access port has a column shape and a needle is inserted into the access port to lead out liquid from a body or introduce liquid into the body. The access port has a solid center portion into which the needle is inserted, and a peripheral portion in a tube shape surrounding the center portion, and the peripheral portion is harder than the center portion.

The peripheral portion can have a tube-shaped inner wall surface formed into a taper shape tapered toward an end along the direction of insertion of the needle, can have a concavo-convex portion formed on at least a portion of an outer circumference surface of the peripheral portion, and can have an outer circumference of the peripheral portion covered with an artificial blood vessel material.

According to another aspect of the present invention, an artificial blood vessel having the access port is provided.

Effect of the Invention

By making the peripheral portion harder than the center portion of the access port, the needle is prevented from being obliquely inserted.

MODES FOR CARRYING OUT THE INVENTION

Figure 1:
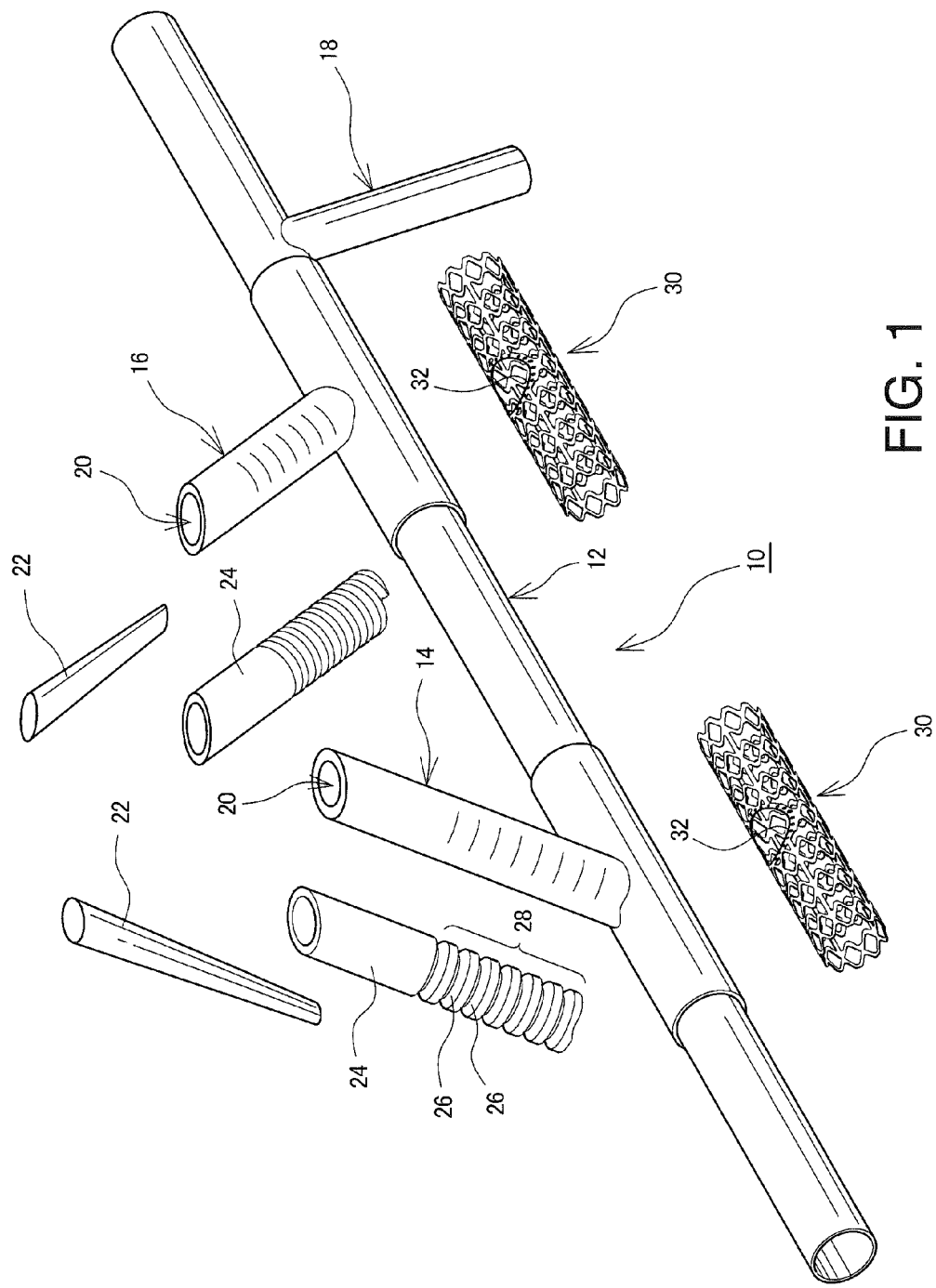
FIG. 1 is a perspective view of an example of an artificial blood vessel having an access port.

Embodiments of the present invention will now be described with reference to the drawings. FIG. 1 is a perspective view of an example of an artificial blood vessel 10 having an access port. This artificial blood vessel 10 is used for blood extracorporeal circulation therapy such as hemodialysis and apheresis in which blood is led out from a body and returned into the body again after a predetermined process is executed. The artificial blood vessel 10 is connected at both ends to blood vessels, especially veins, and includes a trunk portion 12 that acts as a bridge between the veins and branch portions 14, 16, 18 branched from the trunk portion 12. The two branch portions 14, 16 act as connection points with an extracorporeal blood circuit for leading out blood from a body and introducing liquid such as blood into the body, and the other branch portion 18 acts as a shunt connected to an artery. The former two branch portions 14, 16 are referred to as the access branch portions 14, 16 and the later branch portion 18 is referred to as the shunt branch portion 18. The trunk portion 12 and the shunt branch portion 18 are indwelt in the body and portions of the access branch portions 14, 16 are exposed outside the body. The artificial blood vessel 10 can be made of a conventional artificial blood vessel material such as ePTFE (expanded polytetrafluoroethylene) or PTFE (polytetrafluoroethylene).

The trunk portion 12 can be compounded (coated) with SHAp (sintered hydroxyapatite highly-dispersive nanoparticles) about 20 mm from both ends to smoothen joint surfaces between blood vessels of a living body and the artificial blood vessel, thereby improving a patency rate and preventing blood leakage from an initial anastomotic portion at the same time.

An access port 20 is disposed within the access branch portions 14, 16. The access port 20 has a solid column shape, preferably, a cylindrical column shape as a whole, has a length equal to the length of the branch portions 14, 16, and fills the inside of the branch portions 14, 16. Therefore, the branch portions 14, 16 are plugged by the access port 20. The access port 20 has a center portion 22 extending along the axis of the column shape and a tube-shaped peripheral portion 24 surrounding the center portion. In FIG. 1, the center portion 22 and the peripheral portion 24 are separately depicted. The center portion 22 is closely fit inside the tube shape of the peripheral portion 24, thereby forming a solid column shape of the access port 20 as a whole. An intratubular wall of the tube-shaped peripheral portion 24 can be formed into a taper shape tapered toward the end in the direction toward a tip, i.e., the trunk portion 12. The center portion 22 is accordingly formed into a taper shape tapered toward the end.

The taper angle is significantly dependent on a blood vessel of a living body and a position of draw out of the port. Therefore, the taper angle is not limited to the range described above and is changed in design as needed based on a so-called anastomotic position and a distance to the epidermis.

The material of the access port 20 can be an elastic resin material, for example, high compression silicone, and the center portion 22 has a degree of hardness allowing the insertion of a needle, while the peripheral portion is made of silicone having a hardness higher than the center portion 22. Although the degrees of hardness of these silicones are about 10 to 80, the degrees of hardness are not limited to this range.

The peripheral portion 24 has a plurality of annular grooves 26 formed on the outer circumference surface closer to the trunk portion and as a result, a concavo-convex portion 28 having a concavo-convex shape in the axial direction is formed on the outer circumference surface. The concavo-convex portion 28 causes concavo-convex-like shape on the surfaces of the branch portions 14, 16, thereby resulting in favorable compatibility with a living body.

Figure 2:
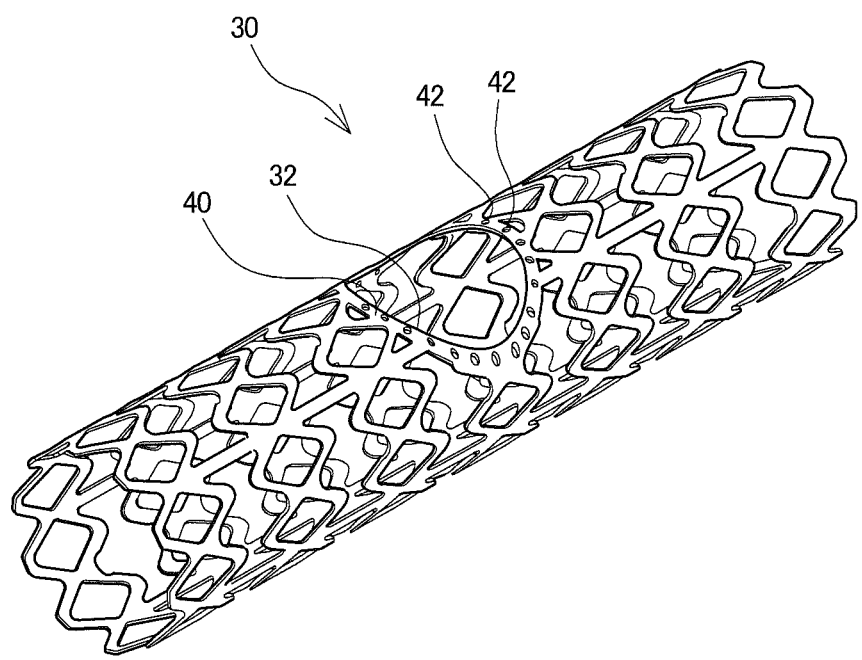
FIG. 2 is a diagram of a detailed shape of a reinforcing member.

A reinforcing member 30 for maintaining the tube shape of the trunk portion 12 is disposed in the trunk portion 12 at a branching position of the branch portions 14, 16 and an adjacent portion. The reinforcing member 30 is sandwiched between artificial blood vessel walls, which are formed as two layers in this portion, and is not exposed outside the artificial blood vessel walls. Therefore, the reinforcing member 30 is not in direct contact with blood and there is no risk of vasoconstriction. The reinforcing member 30 is separately depicted in FIG. 1 and is enlarged in FIG. 2. The reinforcing member 30 has a generally cylindrical shape and a mesh-like structure. The mesh has a shape of combined rhomboids as depicted. Because of the mesh structure, the concavo-convex-like shape of the mesh surface engage with the resin material making up the artificial blood vessel walls, thereby resulting in favorable compatibility thereof. An opening 32 corresponding to the branch portions 14, 16 is disposed on the side surface at substantially the center in the length direction. The material of the reinforcing member 30 can be metal such as stainless steel and nitinol (nickel-titanium alloy).

Figure 3:
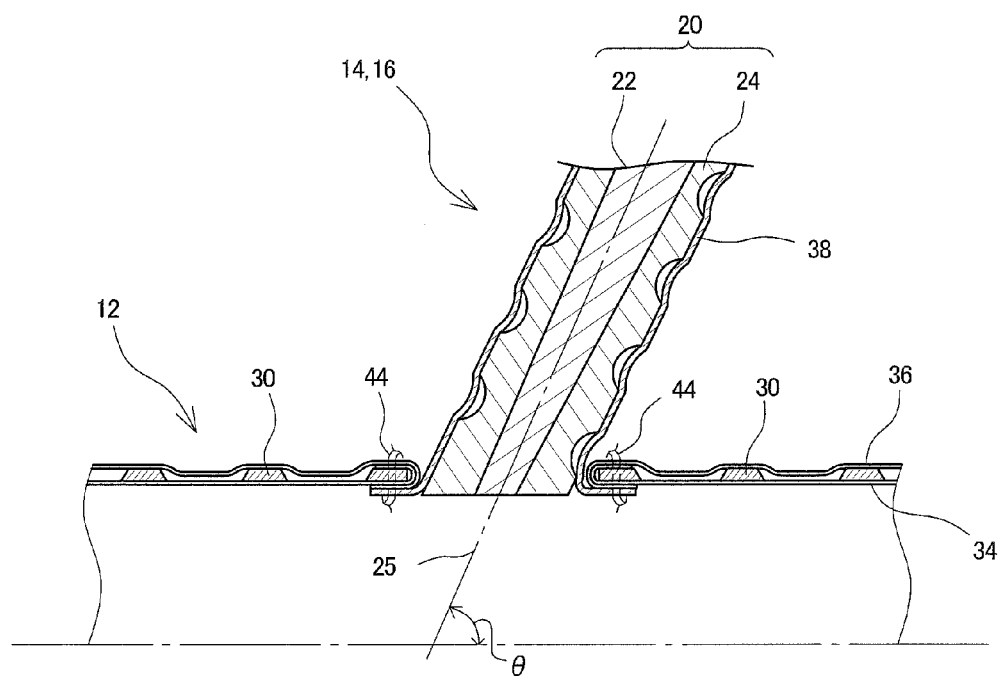
FIG. 3 is a cross-sectional view of a branch portion of the artificial blood vessel.

FIG. 3 is a diagram of a cross section of the branching position of the branch portions 14, 16 from the trunk portion 12 of the artificial blood vessel 10 and the portion adjacent to this position. The branching position and the adjacent portion will hereinafter be referred to as a branching portion. As described above, in the branching portion, the trunk portion 12 is made up of two layers of the artificial blood vessel walls. The inner blood vessel wall and the outer blood vessel wall will be referred to as an inner wall 34 and an outer wall 36, respectively. The reinforcing member 30 is sandwiched between the inner wall 34 and the outer wall 36. The outer wall 36 is slightly longer than the reinforcing member 30 in the axial direction of the trunk portion 12 and closely attached to the inner wall 34 around the entire circumference at both ends, and as a result, the reinforcing member 30 is not exposed. At the edge of the opening 32 of the reinforcing member 30, the inner wall 34 is wrapped toward the outer surface of the reinforcing member and the outer wall 36 is wrapped toward the inner surface of the reinforcing member, and the reinforcing member 30 is not exposed in this portion as well. Therefore, the reinforcing member 30 is completely covered by the inner wall 34 and the outer wall 36. The blood vessel wall 38 of the branch portions 14, 16 has the concavo-convex-like shape formed on the outer surface thereof, reflecting the concavo-convex of the concavo-convex portion 28 formed on the outer circumference surface of the access port 20.

The increase in the surface area of the blood vessel wall 38 increases an area of binding with cells to achieve favorable biocompatibility, and reduces the risk of separation between tissues and the device when stress is applied in the longitudinal direction of the branch portions 14, 16, alleviating a load on the joint portion.

FIG. 3 also depicts a cross section of the access port 20. As depicted, the center portion 22 has a taper shape tapered toward the end and the peripheral portion 24 has the inner wall formed into a taper shape tapered toward the end. As depicted in FIG. 3, the access branch portion 14, 16 is obliquely disposed at an angle θ relative to the trunk portion 12, and in correspondence with this oblique disposition, the leading end portion of the access port 20 is obliquely formed relative to the axis of the access port 20 so as to be coplanar with the inner wall surface of the trunk portion 12. The leading end portion is coplanar with the inner wall surface so as not to form a step. Although the angle θ of the oblique disposition is ideally an angle in the order of 40 to 60 degrees, the angle is significantly dependent on a blood vessel of a living body and a position of draw out of the port. Therefore, the angle θ of the oblique disposition is not limited to the numerical value range described above and is changed in design as needed, based on an anastomotic position of the artificial blood vessel and a distance to the epidermis.

Figure 4:
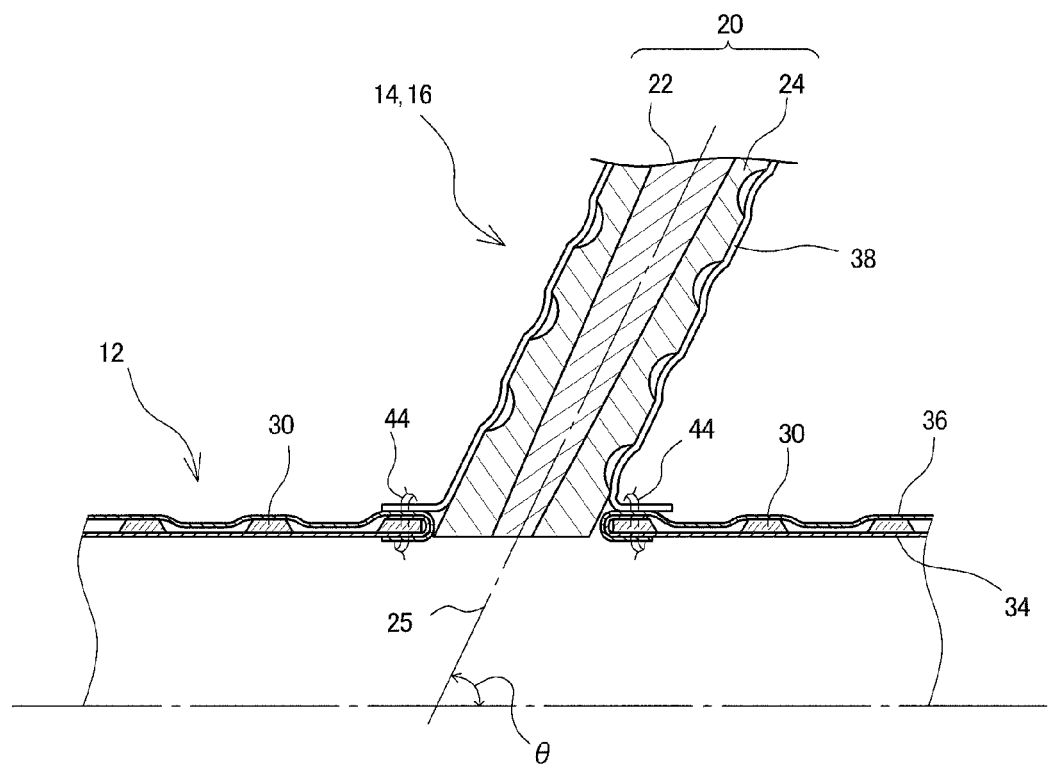
FIG. 4 is a cross-sectional view of the branch portion of the artificial blood vessel.

An annular-shaped annular portion 40 defining the opening 32 of the reinforcing member 30 is disposed with suture holes 42 arranged in the circumferential direction. A suture thread 44 is threaded through the suture holes 42 to sew the inner wall 34 and the outer wall 36, which are the blood vessel walls of the trunk portion 12, and the blood vessel wall 38 of the branch portion together. The blood vessel wall 38 of the branch portion is sewn together on the inner side of the blood vessel walls of the trunk portion. The inner wall 34 and the outer wall 36 are wrapped toward the outer surface and the inner surface, respectively, as described above, and are therefore respectively sewn together outside and inside the annular portion 40. FIG. 4 depicts an example of sewing the blood vessel wall 38 of the branch portion on the outer side of the blood vessel walls of the trunk portion.

Figure 5:
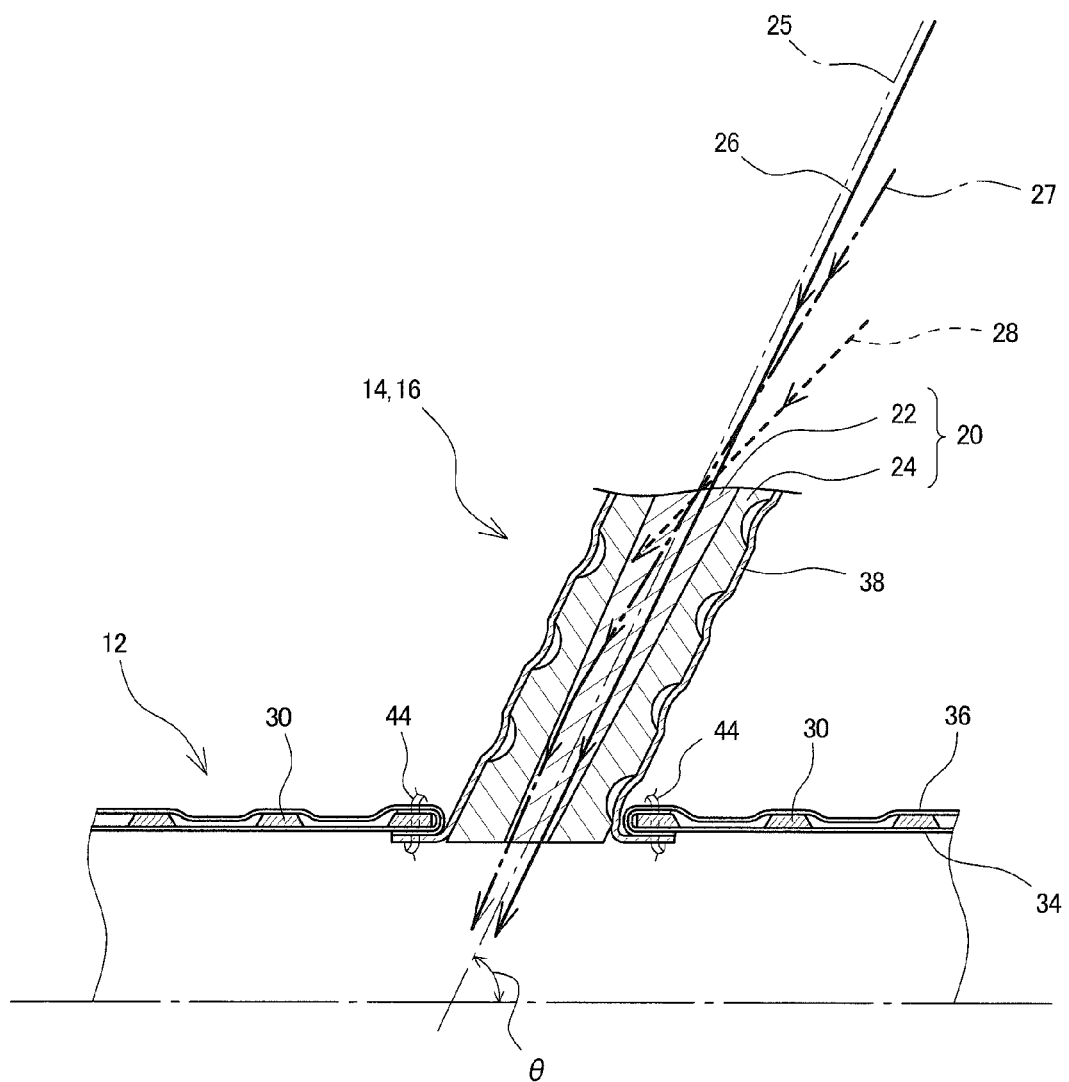
FIG. 5 is an explanatory view of how a needle is inserted into the artificial blood vessel.

As depicted in FIG. 5, a needle is inserted from the upside toward the lower left as indicated by a solid line 26 of FIG. 5, i.e., along an axis 25 of the branch portions 14, 16, from the branch portion 14, 16 toward the trunk portion 12. The center portion 22 has a hardness allowing the insertion of the needle. If the needle is obliquely inserted relative to the axis 25 as indicated by a broken line 28 of FIG. 5, the tip of the needle touches the peripheral portion 24. Since the peripheral portion 24 is harder, the needle is no longer inserted or an operator feels resistance and terminates the insertion of the needle.

If the needle is inserted at a small angle relative to the inner wall surface of the peripheral portion 24 as indicated by a dashed-dotted line 27 of FIG. 5, the tip of the needle touches the inner wall surface of the peripheral portion 24 and then proceeds toward the trunk portion 12 along the inner wall surface of the peripheral portion 24, and the final position of the needle tip is not significantly deviated. Particularly, since the inner wall surface of the peripheral portion 24 has a taper shape tapered toward the end, an area of the region allowing the insertion of the needle is increased on the end at which the needle is inserted (the end outside the body) while the region with the needle projected on the blood vessel side can be limited to a narrower area.

At the time of insertion of the needle, a force pushing the branch portion 14, 16 deeper is applied, and this force acts on the branching portion in such a manner as to collapse the tube shape of the trunk portion 12 from the transverse direction. However, since the branching portion is reinforced by the reinforcing member 30 in the artificial blood vessel 10, the reinforcing member 30 can receive the force from the transverse direction and prevent the trunk portion 12 from being deformed and occluded. Therefore, the reinforcing member 30 has such a stiffness that prevents the trunk portion 12 from being occluded when the force from the transverse direction is applied. The reinforcing member 30 is changed as needed in material, thickness, opening rate of the mesh structure, etc., depending on an estimated value of the force acting from the transverse direction. When the needle is pulled out from the access port 20, the hole opened by the needle is closed due to the elasticity of the center portion 22, returning to the sealed state.

Around the branch portions 14, 16, a cuff can be disposed that is subjected to the flock finishing with a biocompatible material such as SHAp (sintered hydroxyapatite highly-dispersive nanoparticles). Since robust tissue adhesion is achieved between the cuff and subcutaneous fibroblast cells, the infection risk is reduced at the boundary between the branch portions and the skin.

The access port 20 is not limited to the two-layer structure of the soft center portion and the hard peripheral portion and the hardness may be increased in multiple steps or continuously from the center to the outside.

The artificial blood vessel 10 corresponds to a therapy in which blood is once led out from a body and then returned into the body after a predetermined process is executed. If medicinal solution is injected into a blood vessel, this can be supported by forming one access port. In other words, this corresponds to an artificial blood vessel having an access port for injecting medical solution using a left half that includes the branch portion 14 of FIG. 1. If an artificial blood vessel of a simple tube without a branch portion is applied to an arm or a leg, to which force in the transverse direction is frequently applied, the deformation of the blood vessel can be suppressed by disposing the cylindrical reinforcing member.

Although the concavo-convex portion 28 is formed in one portion of the outer circumferential surface of the access port in the example described in this embodiment, this is not a limitation and the concavo-convex portion 28 may be formed in a wider range and may be formed in the entire outer circumferential surface, for example.

Although the access port 20 is formed into the substantially cylindrical shape in the example described in this embodiment, this is not a limitation and a shape with outer diameter increasing toward a body surface portion may be utilized to enable easier access.

Although the trunk portion 12 and the branch portions 14, 16 connected together by sewing in the example described in this embodiment, this is not a limitation and the trunk portion and the branch portion may be connected together by bonding, for example. Although the two-layer structure is used in the blood vessel walls in the portion disposed with the reinforcing member in the described example, this is not a limitation and the two-layer structure may be used in the entire trunk portion 12.

The present invention is not limited to the embodiment described above and includes all alterations and modifications without departing from the technical scope and essential part of the present invention defined by the claims.

EXPLANATIONS OF REFERENCE NUMERALS 10 artificial blood vessel; 12 trunk portion; 14, 16 access branch portion; 18 shunt branch portion; 20 access port; 22 center portion; 24 peripheral portion; and 30 reinforcing member.

The invention claimed is:

1. An access port disposed in a branch portion branched from a trunk portion of an artificial blood vessel, the access port having a solid column shape, comprising:
a solid center portion into which a needle leading out liquid from a body or introducing the liquid into the body is inserted, the solid center portion being disposed along an axis of the column shape; and
a peripheral portion that has a tube shape surrounding the solid center portion, the peripheral portion being harder than the solid center portion, wherein
the solid center portion closely fits inside the tube shape of the peripheral portion, thereby forming a solid column shape of the access port as a whole;
the branch portion is obliquely branched from the trunk portion of the artificial blood vessel; and
a leading end of the access port on the side of the trunk portion is formed oblique to the axis of the solid column shape so as to be coplanar with an inner wall surface of the trunk portion.

2. The access port of claim 1, wherein the peripheral portion has a tube-shaped inner wall surface formed into a taper shape tapered toward an end along a direction of insertion of the needle.

3. The access port of claim 2, wherein the peripheral portion has the concavo-convex portion formed on at least a portion of the outer circumference surface.

4. The access port of claim 3, wherein the peripheral portion has an outer circumference covered by the artificial blood vessel material.

5. The access port of claim 2, wherein the peripheral portion has the outer circumference covered by the artificial blood vessel material.

6. The access port of claim 1, wherein the peripheral portion has a concavo-convex portion formed on at least a portion of an outer circumference surface.

7. The access port of claim 6, wherein the peripheral portion has an outer circumference covered by the artificial blood vessel material.

8. The access port of claim 1, wherein the peripheral portion has an outer circumference covered by an artificial blood vessel material.

9. An artificial blood vessel comprising: the access port of claim 1.

* * * * *